United States Patent
Müller et al.

(10) Patent No.: US 9,101,430 B2
(45) Date of Patent: Aug. 11, 2015

(54) DOUBLE THREADED GUIDANCE OR STIFFENING WIRE FOR MULTIPLE USE VERTEBRAL AUGMENTATION (VA) BALLOON

(75) Inventors: Marc Müller, Weil am Rhein (DE); Kris Chavatte, Küsnacht (CH)

(73) Assignee: DePuy Synthes Products, Inc., Raynham, MA (US)

( * ) Notice: Subject to any disclaimer, the term of this patent is extended or adjusted under 35 U.S.C. 154(b) by 1101 days.

(21) Appl. No.: 12/904,975

(22) Filed: Oct. 14, 2010

(65) Prior Publication Data

US 2012/0095517 A1 Apr. 19, 2012

(51) Int. Cl.
*A61M 29/00* (2006.01)
*A61B 17/88* (2006.01)

(52) U.S. Cl.
CPC .................................. *A61B 17/8855* (2013.01)

(58) Field of Classification Search
CPC ............ A61M 25/10; A61M 25/0102; A61M 25/0169; A61M 25/09041; A61M 25/0905
USPC ............... 600/431, 433, 434, 585; 604/95.03, 604/96.01, 99.01, 99.02, 103, 103.07, 104, 604/107–109; 606/191, 192, 194, 195
See application file for complete search history.

(56) References Cited

U.S. PATENT DOCUMENTS

| | | | |
|---|---|---|---|
| 5,271,415 A * | 12/1993 | Foerster et al. | 600/585 |
| 5,409,470 A * | 4/1995 | McIntyre et al. | 604/528 |
| 6,719,773 B1 | 4/2004 | Boucher et al. | |
| 6,860,901 B1 * | 3/2005 | Baker et al. | 623/1.36 |
| 2004/0102774 A1 | 5/2004 | Trieu | |
| 2007/0173939 A1 | 7/2007 | Kim et al. | |
| 2007/0270876 A1 | 11/2007 | Kuo et al. | |
| 2008/0183204 A1 | 7/2008 | Greenhalgh et al. | |
| 2008/0195207 A1 | 8/2008 | Lin et al. | |
| 2008/0288078 A1 | 11/2008 | Kohm et al. | |
| 2008/0294205 A1 | 11/2008 | Greenhalgh et al. | |
| 2009/0177236 A1 | 7/2009 | Saab et al. | |

(Continued)

FOREIGN PATENT DOCUMENTS

WO    2007/075788 A2    7/2007
WO     2007075788 A2    7/2007

OTHER PUBLICATIONS

International Search Report and Written Opinion, dated Nov. 21, 2011, received from the European Patent Office in connection with International Application No. PCT/US2010/052717.

(Continued)

*Primary Examiner* — Anu Ramana
(74) *Attorney, Agent, or Firm* — Meunier Carlin & Curfman, LLC (57) ABSTRACT

A catheter device that includes a double-threaded guidance wire that allows multiple use of a compliant cavity creation device (i.e., treatment of more than one level). The double-threaded guidance wire may be connected with the luer part of the device and a distal part of the balloon using a threaded engagement to avoid lengthening of the inner tube, avoid lengthening of the balloon, and to limit the plastic deformation of the system in axial direction. In other implementations, the double-threaded guidance wire may be reconnected to the distal part of the balloon with a distal thread of the double-threaded guidance wire in order to restore the nominal length.

20 Claims, 7 Drawing Sheets

(56) References Cited

U.S. PATENT DOCUMENTS

2009/0292323 A1    11/2009  Chirico et al.
2009/0306597 A1*   12/2009  Lupton et al. ............ 604/164.13

OTHER PUBLICATIONS

International Application No. PCT/US20101052717, International Search Report and Written Opinion, mailed Nov. 21, 2011, 18 pages.
Stryker Instruments, "iVAS Inflatable Vertebral Augmentation System" (product sheet), www.stryker.com, Literature No. 1000-025-042, DDM/PS, 2010, 2 ppges.
CareFusion Corporation, "AVAmax Advanced Vertebral Augmentation System" (product sheet), carefusion.com, 2010, 20 pages.
Mager!, F. et al., "A Comprehensive Classification of Thoracic and Lumbar Injuries," European Spine Journal, Springer-Verlag, 1994, vol. 3, pp. 184-201.
Kyphon, Inc., "Advances in Minimally Invasive Spine Therapies: The Mechanics of Balloons Moving Bone," 2004, 8 pages.
Kyphon, Inc, "Verfahrenstechnik Balloon-Kyphoplastie" (product sheet), www.kyphon-eu.com, pp. 1-12.
Kyphon, Inc, "Verfahrenstechnik Balloon-Kyphoplastie" (product sheet), www.kyphon-eu.com, pp. 13-15.
Kyphon, Inc., "KyphX Xpander Inflatable Bone Tamp" (product sheet), www.kyphon.com, 2005, 4 pages.
Kyphon, KyphX Express System, Reducing the Profile. Increasing Your Options, 2004, 2005, 4 pages.
Synthes, Vbs-Vertebral Body Stenting System. Minimally invasive percutaneous, reconstructive treatment for vertebral body fractures. Technique Guide, Feb. 2009, 40 pp.

* cited by examiner

DOUBLE THREADED GUIDANCE OR STIFFENING WIRE FOR MULTIPLE USE VERTEBRAL AUGMENTATION (VA) BALLOON

BACKGROUND

Osteoporosis is a disease that gradually weakens bones and causes them to become brittle. Left untreated, osteoporosis can progress painlessly until a bone breaks. In some cases, osteoporosis can cause compression fractures in the spine. This occurs when the bony block, or vertebral body, in the spine collapses. This causes severe pain, deformity, and loss of height. It can also lead to nerve compression.

Until recently, doctors were limited in how they could treat osteoporosis-related spine fractures. For example, typical options included pain medications, bed rest, bracing or invasive spinal surgery. More recently, the vertebroplasty and kyphoplasty procedures have become available as therapeutic and preventive treatments for compression fractures. Vertebroplasty involves passing a bone needle slowly through the soft tissues of the back to deposit a small amount of orthopedic cement, called polymethylmethacrylate (PMMA) into the vertebral body. PMMA is a medical grade bone cement that has been used for many years in a variety of orthopaedic procedures.

Kyphoplasty is a procedure that involves making small incisions and placing a catheter into the vertebral space where the fracture is located. A cavity is created inside the bone (e.g. drilled) and a balloon, called a bone tamp, is inserted. The balloon may be support by a guidance wire that is passed through a central lumen of the catheter. The balloon is then inflated with contrast medium until it expands to a desired height, deflated and removed. The balloon is used to expand and reposition the compressed bone, and to create a cavity for cement. The cavity created by the balloon may then be filled with PMMA, binding the fracture. Kyphoplasty substantially restores height to the spine, thus reducing deformity (also pain relief).

However, the majority of the balloons utilized by kyphoplasty catheters are made of a ductile (compliant) material. Ductile materials initially undergo elastic (reversible) deformation, followed by plastic (permanent) deformation after reaching a yield point. Therefore, when the balloon is inflated in bone to reduce a fracture, it undergoes some permanent deformation (e.g., deformation of the inner tube and deformation of the balloon). As such, reinflation of the balloon will be biased. Reinserting the guidance wire would result in a non-supported distal balloon part because of the lengthening of the balloon that results from plastic deformation. Therefore, the balloon should not be reused.

SUMMARY

Described herein is a tool that enables multiple use (i.e., reuse) of a catheter for example in a multi-level vertebral augmentation procedure. As described below, the tool may include a balloon catheter that may be a two (or more) lumen catheter. An outer lumen may be used for inflation of the balloon and an inside lumen for guiding a double-threaded guidance wire. A thread in the distal part of the guidance wire may be provided with outer diameter of the distal thread being less than the inner diameter of an inner tube of the catheter. The construction of the thread (i.e., outer diameter, inner diameter, flank lead, length) can be standard design (ISO, Metric) or any design allowing a locking mechanism. The counter piece (e.g., a distal threaded nut) for the distal thread of the guidance wire may be disposed inside the balloon of the catheter and connected to the inner tube. This nut can also be used as a radiopaque marker inside the balloon.

The guidance wire may also have a proximal thread with an outer diameter greater than an outer diameter distal thread. The construction of the thread (e.g., outer diameter, inner diameter, flank lead, length) can be standard design (ISO, Metric) or any design allowing a locking mechanism. The counter piece (e.g., a proximal threaded nut) for the proximal thread of the guidance wire may be disposed inside a luer connector (e.g., a connector for balloon inflation) of the catheter and positioned coaxial to the inner tube. The length of the proximal threaded nut may be longer than the distal threaded nut to account for changes of the balloon catheter during inflation.

In one implementation, the double-threaded guidance wire may remain connected to the balloon during inflation to prevent the balloon and the inner tube from lengthening, substantially avoiding plastic deformation in an axial direction. In another implementation, the double-threaded guidance wire may be removed from the tool during balloon inflation. Thereafter, the double-threaded guidance wire can be reinserted into the tool to connect to the thread in the balloon to restore the pre-inflation nominal balloon axial length and stiffness before inflation. Thus, after first use of the tool, it can be reinserted and used again, as the same catheter length and balloon length is preserved with only minor plastic deformation in axial direction.

In some implementations, there is provided a reusable tool that includes a handle having a proximal thread. A catheter structure may be included that has an outer body and an inner body. The outer body may be connected to a fitting of the handle. An expandable structure may be connected to the outer body, where the expandable structure has a distal thread affixed within an interior thereof. A guidance wire maybe disposed within the inner body, where the guidance wire has a first threaded portion adapted to engage the proximal thread and a second threaded portion adapted to engage the distal thread.

In other implementations, there is provided a reusable tool for treating a vertebral body. The tool may include a handle having an inflation port and a proximal thread. A dual-lumen catheter may be connected to a fitting of the handle and a balloon connected to the outer body. The balloon may have a distal thread affixed within an interior thereof. A guidance wire may be disposed within an inner lumen of the dual-lumen catheter, where the guidance wire has a first threaded portion adapted to engage the proximal thread in the handle and a second threaded portion adapted to engage the distal thread in the balloon.

In yet other implementations, there is provided a tool for treating a vertebral body that includes a handle having an inflation port, a luer fitting and a proximal thread disposed with a body of the handle. A catheter body may be attached to the luer fitting of the handle. A balloon may be connected to the catheter body, where the balloon has a distal thread affixed within an interior thereof. The tool may further include a dual-threaded guidance wire having a first threaded portion adapted to engage the proximal thread and a second threaded portion adapted to engage the distal thread.

In accordance with further implementations there is provided a method for treating bone with a tool having a catheter tube assembly. The method may include fixing a double-threaded guidance wire to a distal threaded nut of an inflatable structure, and deploying the inflatable structure inside a first location of the bone. The inflatable structure may be inflated to create a cavity within a treatment area of the bone, after which the inflatable structure is deflated and removed from inside the bone. The inflatable structure may then be reused and reinserted within the treatment area or inside a second location of the bone.

This summary is provided to introduce a selection of concepts in a simplified form that are further described below in the detailed description. This summary is not intended to identify key features or essential features of the claimed subject matter, nor is it intended that this summary be used to limit the scope of the claimed subject matter. Furthermore, the claimed subject matter is not limited to implementations that solve any or all disadvantages noted in any part of this disclosure.

BRIEF DESCRIPTION OF THE DRAWINGS

To facilitate an understanding of and for the purpose of illustrating the present disclosure, exemplary features and implementations are disclosed in the accompanying drawings, it being understood, however, that the present disclosure is not limited to the precise arrangements and instrumentalities shown, and wherein similar reference characters denote similar elements throughout the several views, and wherein.

DETAILED DESCRIPTION

Referring now to FIGS. 1-6, there is illustrated aspects of a reusable tool 100 that includes a double-threaded guidance or stiffening wire 112. The tool 100 includes a catheter tube assembly 104 made from, e.g., metal or extruded plastic materials. In some implementations, the catheter tube may be generally flexible. The distal end of the catheter tube assembly 104 carries a balloon structure 106, which is made, e.g., from a deformable plastic or other compliant material. In use, the balloon structure 106 is deployed and expanded inside bone, e.g., in a vertebral body, to compact cancellous bone and/or displace cortical bone.

Figure 1:
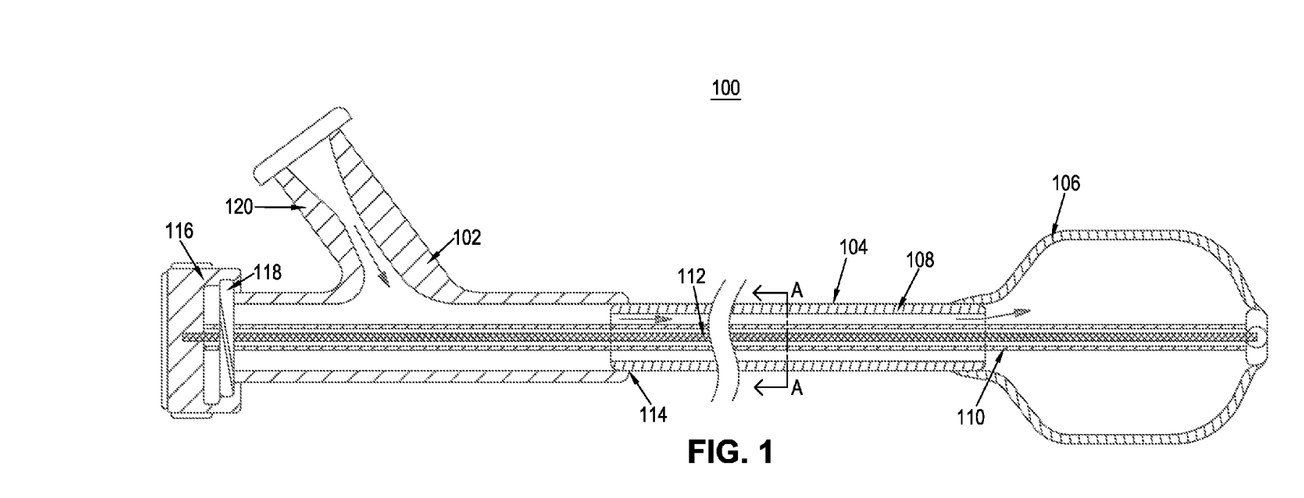
FIG. 1 is a view of a reusable tool having an balloon structure.
Figure 2:
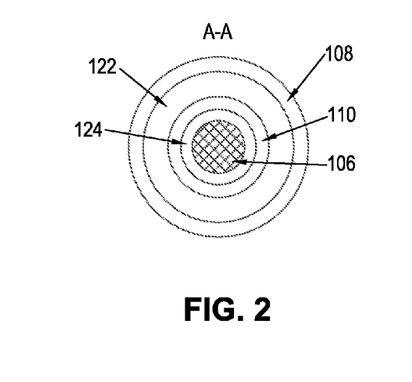
FIG. 2 is a cross-sectional view of a catheter tube assembly of the reusable tool of FIG. 1.

As best shown in FIGS. 1 and 2, the catheter tube assembly 104 includes an outer catheter body 108 and an inner catheter body 110. The inner catheter body 110 extends through and beyond the outer catheter body 108 into the balloon structure 106. The proximal ends of the inner catheter body 110 and the outer catheter body 108 are jointly coupled to the distal end of a luer fitting 114 on a y-shaped luer connector 102, which serves as a handle for the tool 100.

As shown in FIG. 1, the proximal end of the inner catheter body 110 extends within the luer connector 102 beyond the coupled proximal ends of the outer catheter body 108. The extended proximal end of the inner catheter body 110 is coupled to the luer connector 102 at a location proximal to an inflation port 120. The distal end of the inner catheter body 110 extends beyond the distal end of the outer catheter body 108.

The balloon structure 106 is coupled at its proximal end to the distal end of the outer catheter body 108. The balloon structure 106 is coupled at its distal end to the double-threaded guidance wire 112 that extends beyond the distal end of the inner catheter body 110. The double-threaded guidance wire 112 is coupled at its proximal end to a rotatable luer cap 116.

As shown in FIG. 2, the interior diameter of the outer catheter body 108 is larger than the exterior diameter of the inner catheter body 110. An interior passage 122 is thereby defined between them. In use, the interior passage 122 conveys a pressurized flowable medium, e.g., sterile water, radiopaque fluid, gas, or other flowable substance into the balloon structure 106, to expand it. The inflation port 120 on the luer connector 102 (see, e.g., FIG. 1) serves, in use, to couple the interior passage 122 to the source of pressurized flowable medium (not shown). The inner catheter body 110 defines an interior lumen 124 within the interior passage 122. The double-threaded guidance wire 112 extends through the interior lumen 124.

Figure 3:
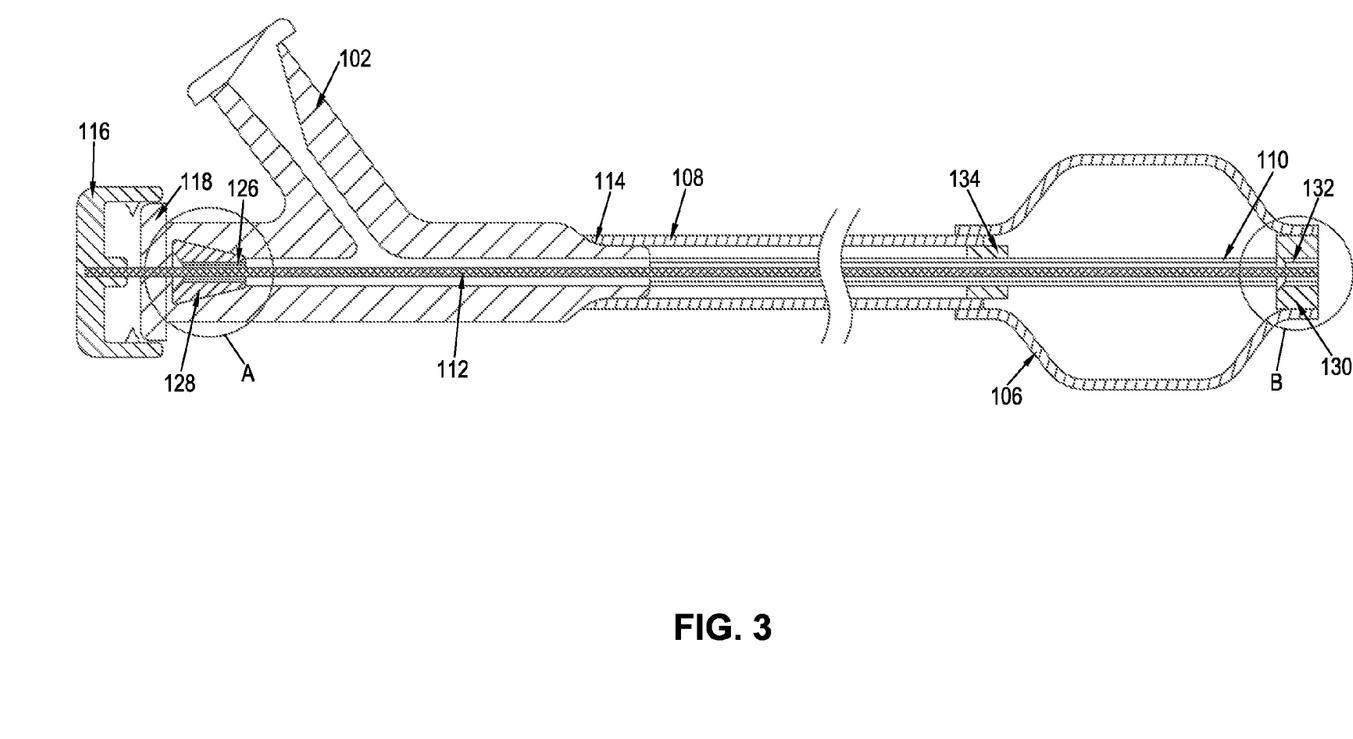
FIG. 3 is a view of the reusable tool of FIG. 1 showing additional details of a double-threaded guidance wire.

With reference to FIGS. 1 and 3, the luer cap 116 rotates about a proximal luer fitting 118 on the luer connector 102. Twisting the luer cap 116 rotates the double-threaded guidance wire 112 within the inner catheter body 110. The torque caused by twisting the luer cap 116 is transmitted to a first threaded portion 126 of the double-threaded guidance wire 112 that engages a proximal threaded nut 128 within the luer connector 102 (see, reference A). The proximal threaded nut 128 may be conical in shape to remain fixed against a pull force of the guidance wire 122 (described below), thus providing a form closure inside the luer connector 102. The proximal threaded nut 128 may also be attached to the luer connector 102 by, e.g., glue, threads, a pin, etc., such that it remains secure.

The torque is also transmitted to a second threaded portion 132 of the double-threaded guidance wire 112 that engages a distal threaded nut 130 within the balloon structure 106 (see, reference B). The distal threaded nut 130 may be used as a radiopaque marker inside the balloon structure 106. A marker 134 may be provided that is fixed to a portion of the inner catheter body 110 that extends within the balloon structure 106. The marker 134 may be a radiopaque marker viewed using plain film x-ray, fluoroscopic x-ray, MRI or CT scanning.

The threads of the nuts 128 and 130, and the guidance wire 112 can be designed both with a left-hand thread or both with a right-hand thread. The threads can also be designed in opposite direction (one left-hand thread and the other right-hand thread). The interaction of the double-threaded guidance wire 112, proximal threaded nut 128, distal threaded nut 130 and the balloon structure 106 is described below with reference to FIGS. 7-10.

Figure 4:
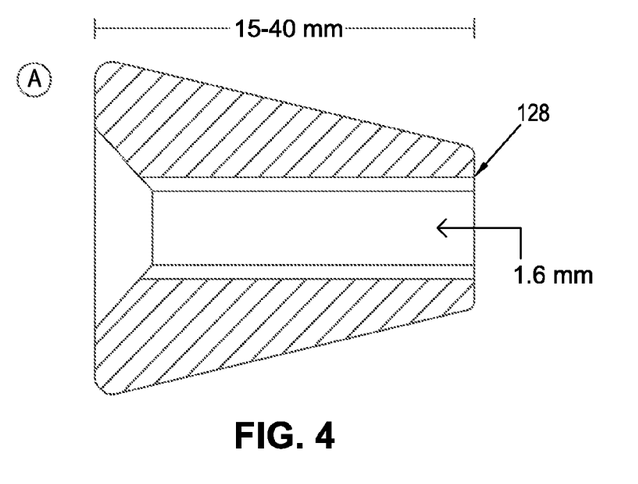
FIG. 4 is a cross-sectional view of a proximal threaded nut.
Figure 5:
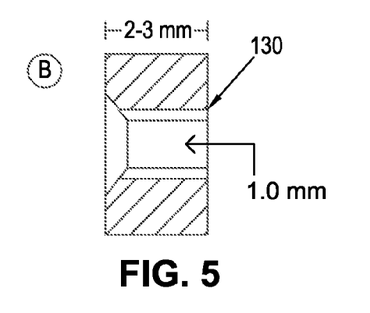
FIG. 5 is a cross-sectional view of a distal threaded nut.
Figure 6:
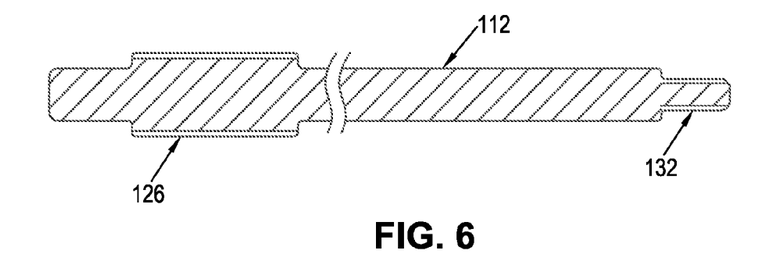
FIG. 6 is a cross-sectional view of the double-threaded guidance wire.

In some implementations, as shown in FIG. 4, the proximal threaded nut 128 may have a length of 15-40 mm. The diameter of the hole of the proximal threaded nut 128 may be approximately 1.6 mm. As shown in FIGS. 3 and 5, the distal threaded nut 130 may be inside the balloon structure 106 and have a length of 2-3 mm. The diameter of the hole of the distal threaded nut 130 may be approximately 1.0 mm.

The material from which the balloon structure 106 is made may possess various physical and mechanical properties to optimize its functional capabilities to compact cancellous bone. Such properties may include the ability to expand in volume, the ability to deform in a desired way when expanding and assume a desired shape inside bone, and/or the ability to withstand abrasion, tearing, and puncture when in contact with cancellous and/or cortical bone.

When compressing cancellous bone and/or creating a cavity, the expanded shape inside bone may be selected to optimize the formation of a cavity that, when filled with a selected material (e.g., PMMA, calcium phosphate, bone chips, etc.), provides support across the region of the bone being treated. In cases where the bone disease causing fracture is the loss of cancellous bone mass, as in osteoporosis, the selection of the shape of the balloon structure 106 inside bone may take into account the cancellous bone volume which should be compacted to achieve the desired therapeutic result. Another consideration for the selection of the shape of the balloon structure 106 is the amount that the targeted fractured bone region has been displaced or depressed. For example, the balloon structure 106 may have a predetermined length, such as 10 mm, 15 mm or 20 mm, selected based on the amount of displacement. The expansion of the balloon structure 106 inside a bone can elevate or push the fractured cortical wall back to or near its anatomic position occupied before fracture occurred.

Figure 7:
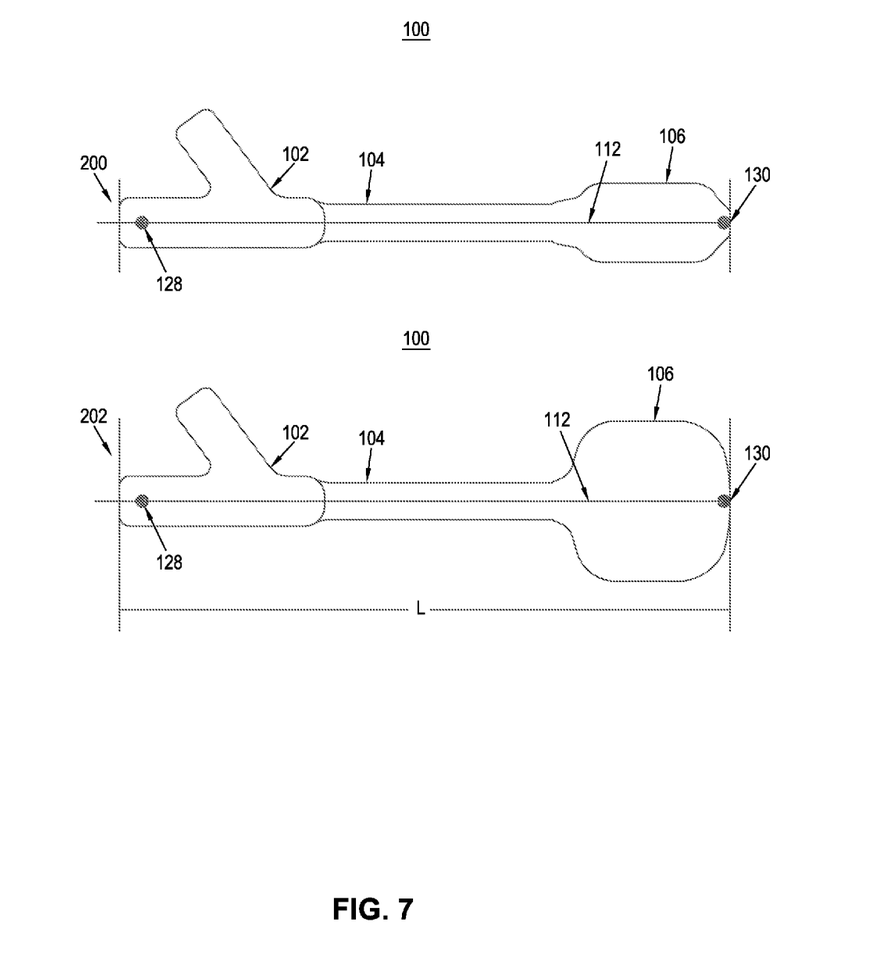
FIG. 7 illustrates an implementation to inflate the balloon structure with the double-threaded guidance wire attached thereto.
Figure 8:
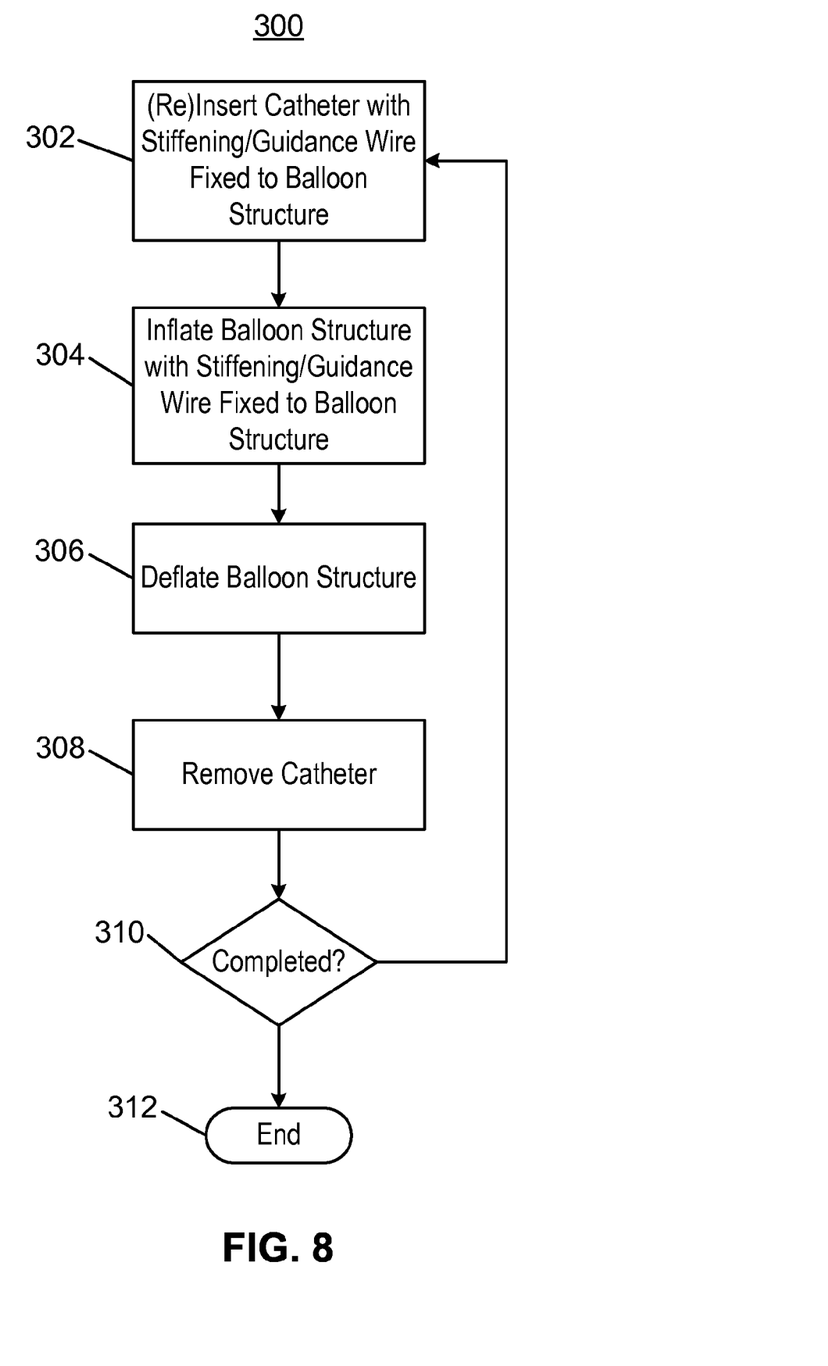
FIG. 8 is operational flow diagram of exemplary processes that are performed as part of a procedure using the implementation of FIG. 7.

Referring now to FIG. 7, there is illustrated an implementation of the tool 100 wherein the double-threaded guidance wire 112 remains fixed to the balloon structure 106 during inflation of the balloon structure 106. FIG. 8 illustrates an associated operational flow diagram 300 of exemplary processes that are performed as part of a procedure using the tool 100 in such an implementation. At 302, when the catheter tube assembly 104 of the tool 100 is delivered into a patient, the double-threaded guidance wire 112 is fixed to the distal threaded nut 130 of the balloon structure 106 (see, reference 200). In the delivered state, the balloon structure 106 may be folded such that the tool 100 has an axial length L.

At 304, the balloon structure 106 is then inflated with the double-threaded guidance wire 112 fixed to the distal threaded nut 130 (see, reference 202). The inflation of the balloon structure 106 may, e.g., compress or create a cavity within cancellous bone and/or elevate the cortical wall of the spine. As shown at 202, the tool 100 substantially remains at the axial length L in the inflated state.

At 306, the balloon structure 106 is then deflated and the catheter tube assembly 104 may be removed at 308. Because the double-threaded guidance wire 112 remains fixed to the balloon structure 106 through the threaded engagement of the second threaded portion 132 to the distal threaded nut 130, the balloon structure 106 remains substantially at its original axial length L.

At 310, if the procedure using the tool 100 is completed, then the process ends 312. However, if the procedure involves further balloon inflations, then at 310, the catheter tube assembly 104 may be reused and reinserted (at 302) and the balloon structure 106 reinflated for subsequent use. Thus, the tool 100 may be reused either in the same vertebral body or another vertebral body in the same patient because the balloon structure 106 remains supported by the double-threaded guidance wire 112 and, as such, has a known size.

Figure 9:
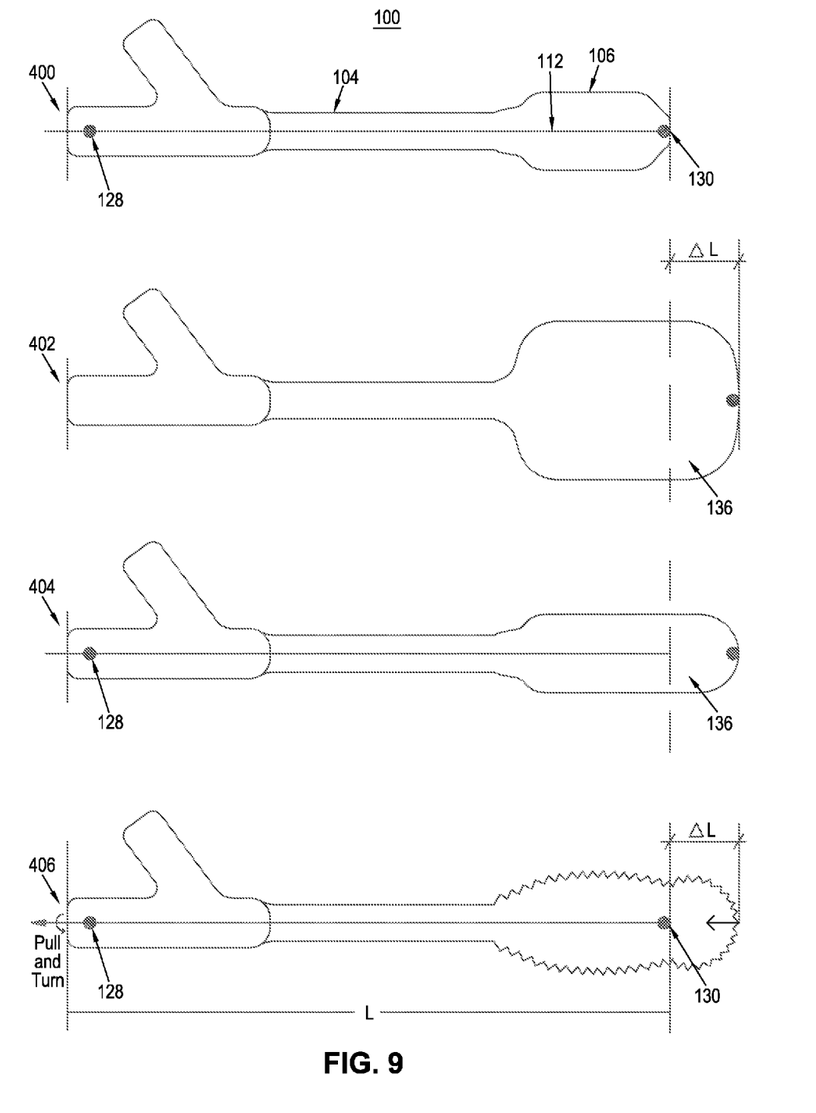
FIG. 9 illustrates an implementation to inflate the balloon structure where the double-threaded guidance wire is removed during inflation of the balloon structure and reinserted to withdraw the balloon structure.
Figure 10:
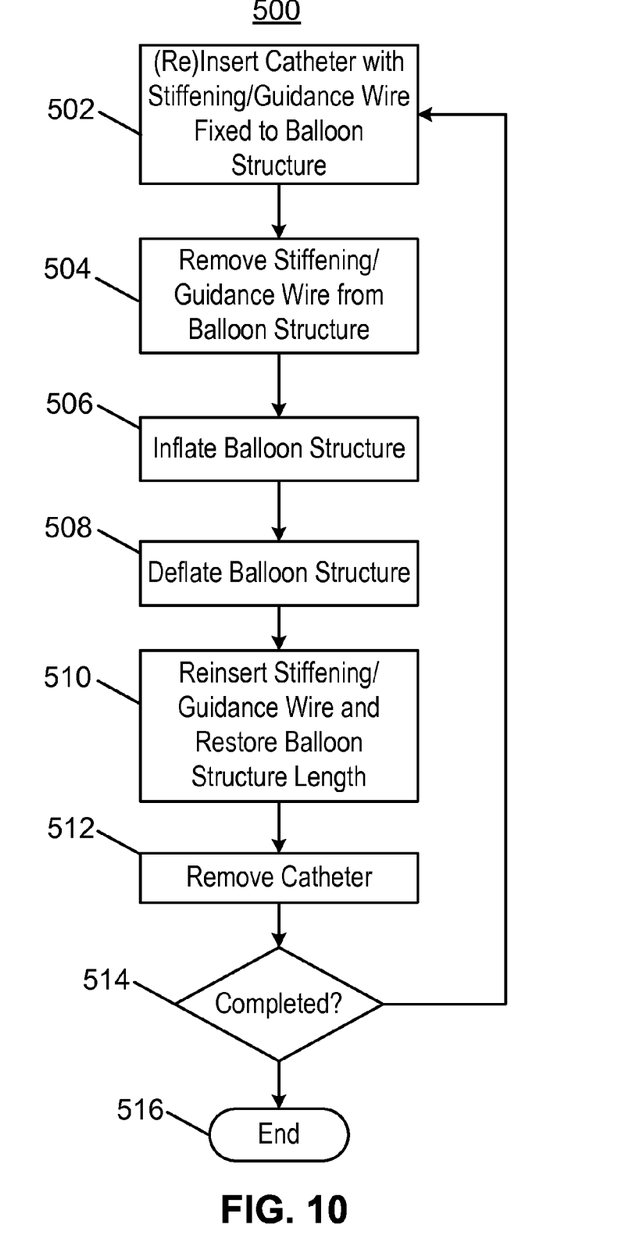
FIG. 10 operational flow diagram of exemplary processes that are performed as part of a procedure using the implementation of FIG. 9.

Referring now to FIG. 9, there is illustrated an implementation wherein the double-threaded guidance wire 112 is removed from the balloon structure 106 during inflation of the balloon structure 106. FIG. 10 is an associated operational flow diagram 500 of exemplary processes that are performed as part of a procedure using the tool 100 in such an implementation. At 502, when the catheter tube assembly 104 of the tool 100 is delivered into a patient, the double-threaded guidance wire 112 is fixed to the distal threaded nut 130 of the balloon structure 106 (see, reference 400). In the delivered state, the balloon structure 106 may be folded.

At 504, the double-threaded guidance wire 112 is removed, and the balloon structure 106 is then inflated at 506 (see, reference 402). The inflation of the balloon structure 106 compresses or creates a cavity within cancellous bone and/or elevates the cortical wall. The inflation of the expanding balloon structure 106 also expands the balloon structure 106 in the axial direction by an amount (designated by ΔL) to create an expansion area 136 that is unsupported.

At 508, the balloon structure 106 is then deflated and the double-threaded guidance wire 112 is reinserted into catheter tube assembly 104 at 510 (see, reference 404). For example, the double-threaded guidance wire 112 may be rotated such that the second threaded portion 132 engages the distal threaded nut 130 in the balloon structure 106. As shown in reference 406, the double-threaded guidance wire 112 is pulled back to engage the first threaded portion 126 within the proximal threaded nut 128. As such, the length of the balloon structure 106 is restored to the original starting position, as indicated by the arrows and dashed lines.

At 512, the catheter tube assembly 104 may be removed. At 514, if the procedure using the tool 100 is completed, then the process ends 516. However, if the procedure involves further balloon inflations, then at 514, the catheter tube assembly 104 may be reinserted (at 502) and the process repeats for the subsequent insertion(s). The tool 100 may be reused either in the same vertebral body or another vertebral body in the same patient.

In the implementations above, the interaction of the double-threaded guidance wire 112, proximal threaded nut 128 and distal threaded nut 130 locks the guidance wire 112 into a position such that the balloon structure 106 is returned to its original length after inflation. It is noted that any locking mechanism that returns the balloon structure 106 its original length after inflation may be used in the tool 100.

Although the distal threaded nut 130 has been described as being within the balloon structure 106, the distal threaded nut may be either inside or outside of the balloon structure 106. For example, the thread may be part of a rivet that is outside the balloon structure 106 and forms part of a tip of the balloon structure 106.

The subject matter described above is provided by way of illustration only and should not be construed as limiting. Various modifications and changes may be made to the subject matter described herein without following the example embodiments and applications illustrated and described, and without departing from the true spirit and scope of the present invention, which is set forth in the following claims.

What is claimed is:

1. A reusable tool, comprising:
   a handle having a proximal thread;
   a catheter structure having an outer body and an inner body, the outer body being connected to the handle;
   an expandable structure connected to the outer body, the expandable structure having a distal thread affixed within an interior thereof; and
   a guidance wire disposed within the inner body, the guidance wire having a first threaded portion adapted to engage the proximal thread and a second threaded portion adapted to engage the distal thread.

2. The tool according to claim 1, the handle further comprising a rotatable cap, wherein rotation of the rotatable cap transfers torque to the guidance wire to engage the second threaded portion with the distal thread.

3. The tool according to claim 2, wherein the guidance wire is retracted from the tool and rotated by the rotatable cap to engage the first threaded portion with the proximal thread.

4. The tool according to claim 3, wherein engagement of the second threaded portion with the distal thread is by one of left-handed threads and right-handed threads, and
wherein engagement of the first threaded portion with the proximal thread is by one of left-handed threads and right-handed threads.

5. The tool according to claim 1, wherein the handle comprises a y-connector to provide an inflation port to the tool.

6. The tool according to claim 5, wherein a pressurize flowable medium is provided to the inflation port, the pressurized flowable medium passing through an interior passage between the outer body and the inner body to expand the expandable structure.

7. The tool according to claim 6, wherein the expandable structure is expanded with the second threaded portion of the guidance wire engaged with the distal thread, and wherein the expandable structure remains substantially at a before-inflation length L along an axial direction after being pressurized by flowable medium.

8. The tool according to claim 6, wherein the expandable structure is expanded with the guidance wire removed from the tool, and wherein the expandable structure extends a length ΔL greater than a before-inflation length along an axial direction after being pressurized by the flowable medium.

9. The tool according to claim 8, wherein the guidance wire is reinserted into the tool to engage second threaded portion with the distal thread after the expandable structure is deflated, and wherein retraction of the guidance wire to engage the first threaded portion with the proximal thread substantially returns the expandable structure to the before-inflation length along the axial direction.

10. The tool according to claim 1, wherein the proximal thread has a length between 15-40 mm and a thread size of approximately 1.6 mm.

11. The tool according to claim 1, wherein the distal thread has a length between 2-3 mm and a thread size of approximately 1.0 mm.

12. A reusable tool for treating a vertebral body, comprising:
a handle having an inflation port and a proximal thread;
a dual-lumen catheter connected to the handle, the dual-lumen catheter having an outer body;
a balloon connected to the outer body, the balloon having a distal thread affixed within an interior thereof; and
a guidance wire disposed within an inner lumen of the dual-lumen catheter, the guidance wire having a first threaded portion adapted to engage the proximal thread in the handle and a second threaded portion adapted to engage the distal thread in the balloon.

13. The tool according to claim 12, wherein a pressurized flowable medium is provided to the inflation port, the pressurized flowable medium passing through an outer lumen of the dual-lumen catheter to expand the balloon.

14. The tool according to claim 13, wherein the balloon is expanded with the second threaded portion of the guidance wire engaged with the distal thread to maintain the balloon substantially at its uninflated length along an axial direction.

15. The tool according to claim 13, wherein the balloon is expanded with the guidance wire removed from the tool, and wherein the balloon extends a length ΔL from its uninflated length along the axial direction after being pressurized by the flowable medium.

16. The tool according to claim 12, wherein the guidance wire is reinserted into the tool to engage second threaded portion with the distal thread after the balloon is deflated, and wherein retraction of the guidance wire to engage the first threaded portion with the proximal thread returns the balloon to its uninflated length along the axial direction.

17. The tool according to claim 12, wherein the proximal thread has a length between 15-40 mm and a thread size of approximately 1.6 mm.

18. The tool according to claim 12, wherein the distal thread has a length between 2-3 mm and a thread size of approximately 1.0 mm.

19. A tool for treating a vertebral body, comprising:
a handle having an inflation port, a luer fitting and a proximal thread disposed within a body of the handle;
a catheter body that attaches to the luer fitting of the handle;
a balloon connected to the catheter body, the balloon having a distal thread affixed within an interior thereof; and
a threaded guidance wire having a first threaded portion adapted to engage the proximal thread and a second threaded portion adapted to engage the distal thread.

20. The tool according to claim 19, wherein the balloon is inflated by a pressurize flowable medium provided to the inflation port, and wherein after the balloon is deflated, the second threaded portion of the dual-threaded guidance is engaged with the distal thread wire to return the balloon to a length along an axial direction before inflation.

* * * * *